United States Patent [19]

Verbeek

[11] Patent Number: 5,630,830
[45] Date of Patent: May 20, 1997

[54] DEVICE AND METHOD FOR MOUNTING STENTS ON DELIVERY SYSTEMS

[75] Inventor: Marcel A. E. Verbeek, Geleen, Netherlands

[73] Assignee: Medtronic, Inc., Minneapolis, Minn.

[21] Appl. No.: 631,750

[22] Filed: Apr. 10, 1996

[51] Int. Cl.$^6$ .................................. A61M 29/00
[52] U.S. Cl. .................. 606/198; 606/108; 606/192
[58] Field of Search .................... 606/192, 194, 606/198, 108, 191; 604/96

[56] References Cited

U.S. PATENT DOCUMENTS

| | | | |
|---|---|---|---|
| 3,382,872 | 5/1968 | Rubin | 128/214.4 |
| 3,677,244 | 7/1972 | Hassinger | 128/214.4 |
| 3,877,429 | 4/1975 | Rasumoff | 128/214.4 |
| 4,166,469 | 9/1979 | Littleford | 128/784 |
| 4,243,050 | 1/1981 | Littleford | 128/784 |
| 4,345,606 | 8/1982 | Littleford | 128/784 |
| 4,830,003 | 5/1989 | Wolff et al. | 606/191 |
| 4,913,141 | 4/1990 | Hillstead | 606/108 |
| 5,026,377 | 6/1991 | Burton et al. | 606/108 |
| 5,108,416 | 4/1992 | Ryan et al. | 606/194 |
| 5,158,548 | 10/1992 | Lau et al. | 604/96 |
| 5,190,058 | 3/1993 | Jones et al. | 128/898 |
| 5,192,297 | 3/1993 | Hull | 606/195 |
| 5,201,757 | 4/1993 | Heyn et al. | 606/198 |
| 5,226,889 | 7/1993 | Sheiban | 604/101 |
| 5,242,399 | 9/1993 | Lau et al. | 604/104 |
| 5,266,073 | 11/1993 | Wall | 623/1 |
| 5,306,294 | 4/1994 | Winston et al. | 623/1 |
| 5,338,296 | 8/1994 | Dalessandro et al. | 604/96 |
| 5,344,426 | 9/1994 | Lau et al. | 606/198 |
| 5,360,401 | 11/1994 | Turnland | 604/96 |
| 5,368,566 | 11/1994 | Crocker | 604/101 |
| 5,387,235 | 2/1995 | Chuter | 623/1 |
| 5,391,172 | 2/1995 | Williams et al. | 606/108 |

OTHER PUBLICATIONS

Rupp, et al., Patent Application "Stent Mounting and Transfer Device and Method", filed Dec. 21, 1995, USSN 08/576, 720.

*Primary Examiner*—Michael Buiz
*Assistant Examiner*—Kevin Truong
*Attorney, Agent, or Firm*—John R. Duncan; Dianne M. F. Plunkett; Harold R. Patton

[57] ABSTRACT

A device for mounting a stent on a delivery system such as a balloon catheter and methods of making and using the device. Typically, the device includes an elongated, preferably transparent body having an axial aperture and two axial grooves in the outside surface. A stent is located in the axial aperture, preferably in a correspondingly configured recess. A sleeve of low friction, preferably transparent, material is situated inside the stent with the stent in tension on the sleeve. To mount the stent on the a balloon catheter or the like, the balloon is inserted into the sleeve with the balloon preferably in compression. The position of the balloon within the device is visible through the sleeve and body. The sleeve is pulled out of the aperture, then the body is split along the grooves and removed. Typically, the device is made by placing a tubular sleeve of low friction material over a pin, placing a stent in tension over the sleeve, forming two body halves having cooperating grooves, bringing the body halves together to form an axial aperture over said stent, bonding the two body halves together and removing the pin.

21 Claims, 3 Drawing Sheets

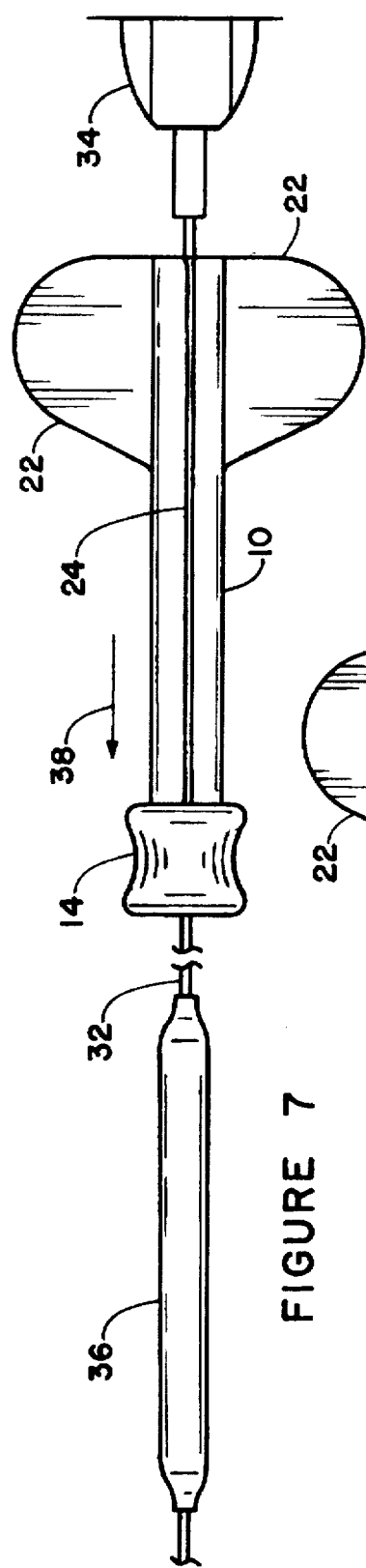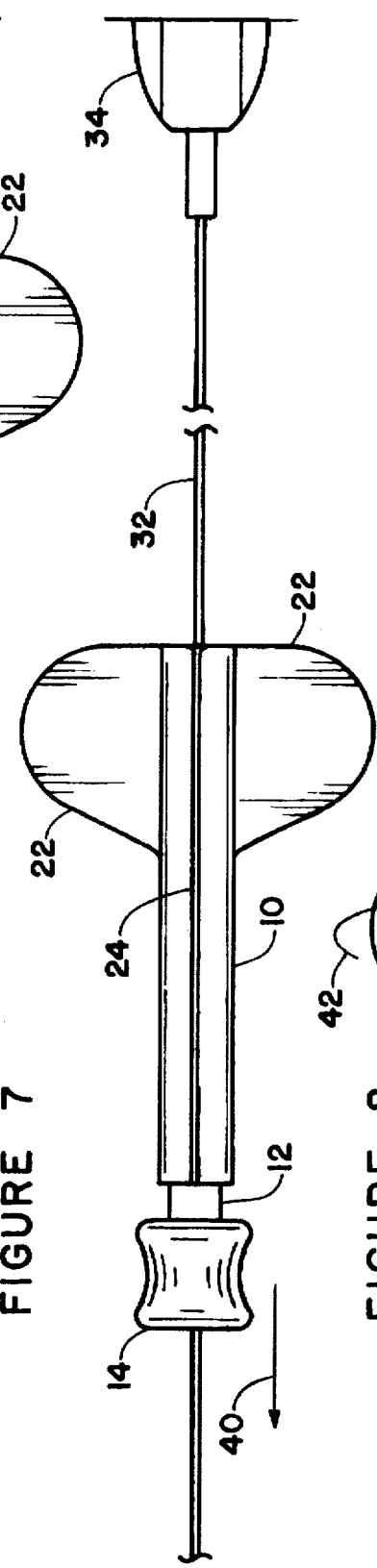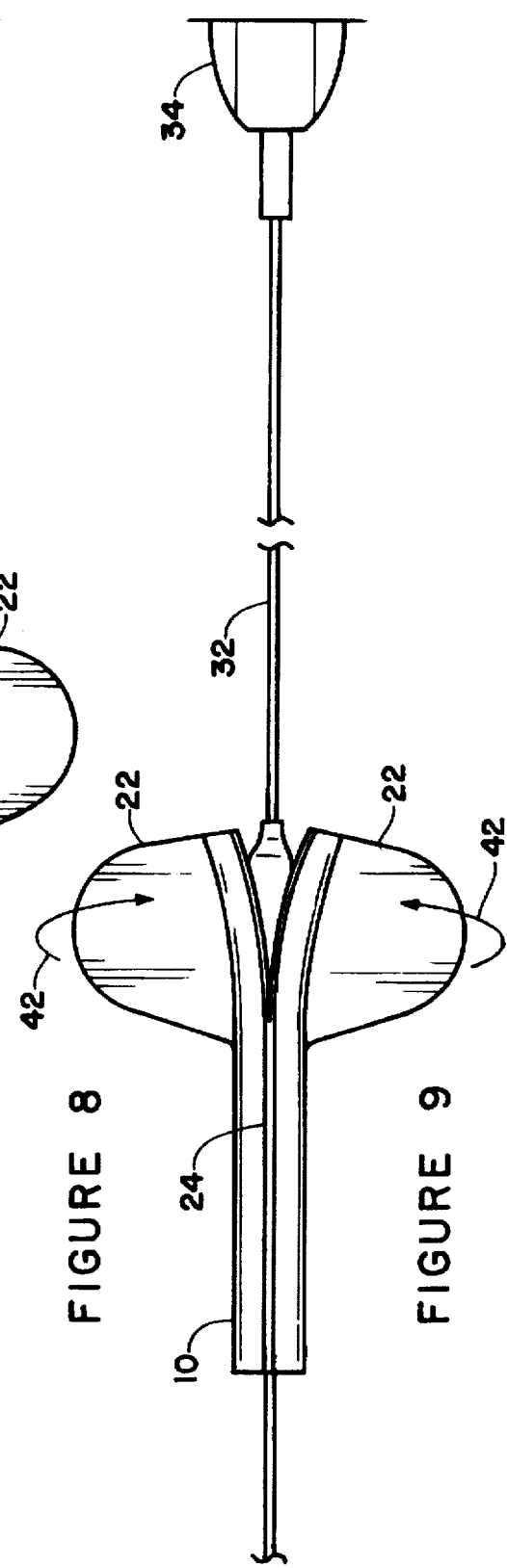

DEVICE AND METHOD FOR MOUNTING STENTS ON DELIVERY SYSTEMS

FIELD OF THE INVENTION

This invention relates in general to intervascular stent implants for maintaining vascular patency in humans and animals and more particularly to a method and tool assembly for supporting a stent and for transferring the stent to a delivery system such as a balloon catheter.

BACKGROUND OF THE INVENTION

Percutaneous transluminal coronary angioplasty (PTCA) is used to reduce arterial build-up of cholesterol fats or atherosclerotic plaque. Typically a guidewire is steered through the vascular system to the site of therapy. A guiding catheter, for example, can then be advanced over the guidewire and a balloon catheter advanced within the guiding catheter over the guidewire. The balloon at the distal end of the catheter is inflated causing the site of the stenosis to widen. The dilatation of the occlusion, however, can form flaps, fissures and dissections which threaten re-closure of the dilated vessel or even perforations in the vessel wall. Implantation of a metal stent can provide support for such flaps and dissections and thereby prevent reclosure of the vessel or provide a patch repair for a perforated vessel wall until corrective surgery can be performed. Reducing the possibility of restenosis after angioplasty reduces the likelihood that a secondary angioplasty procedure or a surgical bypass operation will be necessary.

An implanted prosthesis such as a stent can preclude additional procedures and maintain vascular patency by mechanically supporting dilated vessels to prevent vessel collapse. Stents can also be used to repair aneurysms, to support artificial vessels as liners of vessels or to repair dissections. Stents are suited to the treatment of any body lumen, including the vas deferens, ducts of the gallbladder, prostate gland, trachea, bronchus and liver. The body lumens range in size from the small coronary vessels to the 30 mm aortic vessel. The invention applies to acute and chronic closure or reclosure of body lumens.

A stent typically is a cylindrically shaped device formed from wires or a slotted tube and intended to act as a permanent prosthesis. A stent is deployed in a body lumen from a radially compressed configuration into a radially expanded configuration which allows it to contact and support a body lumen. The stent can be made to be radially self-expanding or expandable by the use of an expansion device. The self expanding stent is made from a resilient springy material while the device expandable stent is made from a material which is plastically deformable. A plastically deformable stent can be implanted during a single angioplasty procedure by using a balloon catheter bearing a stent which has been crimped onto the balloon. Stents radially expand as the balloon is inflated, forcing the stent into contact with the body lumen thereby forming a supporting relationship with the vessel walls. Deployment is effected after the stent has been introduced percutaneously, transported transluminally and positioned at a desired location by means of the balloon catheter.

The stainless-steel or tantalum mesh stent that props open blocked coronary arteries, keeps them from reclosing after balloon angioplasty. A balloon of appropriate size and pressure is first used to open the lesion. The process is repeated with a stent crimped on a balloon. The stent is deployed when the balloon is inflated. The stent remains as a permanent scaffold after the balloon is withdrawn.

A number of different stent structures and placement instruments have been developed. For example, Wall in U.S. Pat. No. 5,266,073 describes a rolled tubular stent carried at the end of a tubular catheter with a second catheter threaded therethrough to carry a balloon. The assembly is inserted into an artery until the stent is at the proper location, then the balloon catheter is positioned within the stent and expanded to expand, unroll and lock the stent. This arrangement usually requires an undesirably large diameter catheter for carrying the stent and includes a complex and possibly unreliable locking method for holding the stent in the expanded position. Also, non-uniform stent expansion may occur, since the expanding balloon cannot directly contact the portion of the stent that overlaps its carrier catheter.

Other stent delivery systems have a self-expanding stent compressed in a tube, such as that described by Burton et al. in U.S. Pat. No. 5,026,377. The tube is inserted until the stent is in the desired location and the stent is forced from the tube and expands into contact with the vessel wall. A balloon catheter may be inserted and expanded to further expand the stent. Problems may arise with maintaining the partially expanded stent in position and preventing pushing the stent out of position during insertion of the balloon catheter.

Others have used a rolled tubular stent placed around a balloon catheter and covered by a tubular sheath connected to a guidewire extending through the catheter, such as is described by Lau et al. in U.S. Pat. No. 5,158,548. The assembly is inserted in to a desired location in a body lumen, the sheath is moved longitudinally by the guidewire away from the stent and the balloon is expanded to expand the stent. This requires a complex tubular catheter, sheath and stent assembly.

Balloon catheters are available with a stent preloaded around the balloon. This requires a second balloon catheter to be used to dilate the lesion enough to allow the stent to enter. Subsequently, the catheter bearing the stent is introduced and the stent emplaced. This requires the use of two expensive catheters to complete placement of the stent and two catheterization.

Loose stents are available which users simply slip over a balloon catheter and crimp against the catheter balloon with the fingers. While this arrangement is simple and quick, the stent may be damaged during storage and handling prior to use, while it is being placed over the catheter balloon or during the crimping step. Damaged stents cannot be used. If damage to the stent is not noticed, the stent may not perform as intended in use. Further, depending on the type of delivery system, fitting the stent over the delivery end without damage is sometimes difficult.

Excellent methods and apparatus for mounting stents on catheter balloons and the like are described by Rupp et al. in U.S. patent application Ser. No. 08/576,720, filed Dec. 21, 1995, now pending and assigned to the assignee of this application. While the methods and apparatus described in that application provide excellent results, I have found that in some instances a disposable mounting device is preferable.

Thus, there is a continuing need for improved devices and methods for mounting a stent onto a delivery system such as a balloon catheter that are simpler, less expensive, more convenient, more reliable, avoid damage to the stent and include a sterile, disposable, mounting device to avoid contact between a sterile stent and catheter and a non-sterile surface.

SUMMARY OF THE INVENTION

The above-noted problems, and others, are overcome in accordance with this invention by a stent mounting device comprising an elongated body formed from two, usually identical, halves bonded together. The body has an axial aperture in which a stent is retained. A low friction sleeve member is inserted into the axial aperture for receiving a delivery system, such as a balloon catheter. In addition, the invention includes a method of making such a device and a method of mounting a stent on a delivery system with the device.

The stent mounting device basically consists of two body halves each having a longitudinal recess on mating surfaces. The mating surfaces are bonded together with a stent in one recess. The stent is held in place in the axial aperture formed when the two recesses abut. Preferably, shallow channels are formed in the wall of the axial aperture to fit the stent configuration and help hold the stent in place. For example, with Wiktor stents, a shallow, relatively wide, helical channel would be appropriate.

In order to place a stent into the aperture, the stent is mounted on a sleeve that is placed in the recess in one body half before the body halves are bonded together. The sleeve is formed from a thin, low friction material such as tetrafluroethylene and has an outside diameter corresponding substantially to the inside diameter of the body axial aperture. The sleeve has a handle or knob formed on one end abutting an end of the body aperture for removal of the sleeve. The stent is placed over the sleeve and a pin having a diameter substantially the same as the sleeve internal diameter is inserted into the pin to support the sleeve. Preferably the stent diameter is slightly less than the outside diameter of the sleeve so as to be held in place by stent resiliency. The assembly of pin, sleeve and stent is placed between the body halves with the stent aligned with the aperture internal channel and the knob just outside an end of the axial aperture.

The body halves are bonded together in any suitable manner, such as adhesive, ultrasonic, or thermal bonding. Once bonding is complete, the pin is slipped out of the sleeve.

A delivery system, such as a catheter carrying a wrapped balloon, is slipped into the sleeve and aligned with the stent. Preferably, the body and sleeve are formed from a transparent material so that the position of the delivery system in the device can be observed. The delivery system is inserted through a hole in the sleeve knob that is coaxial with the sleeve. Since the delivery system, (e.g. a balloon catheter) is preferably slightly compressible and slightly greater in diameter that the inside sleeve diameter, the hole in the sleeve knob is preferably conical to compress the delivery system during insertion.

Once insertion is complete, the sleeve is pulled from between the stent and the delivery system. The stent contracts slightly and the delivery system expands slightly, so that the two are held tightly together.

A V-shaped groove is preferably provided along two opposite sides of the body and two outwardly extending tabs are formed between the grooves so that the tabs can be grasped and pulled apart to split the body apart to release the stent mounted on the delivery system. Preferably, the body is formed from a longitudinally oriented plastic material that preferentially splits in the longitudinal direction. Typical such materials include mixtures of polyurethane and polycarbonate. The delivery system with mounted stent is now ready for use.

In conventional practice, to repair a lesion in a bodily vessel, generally one balloon catheter is inserted and expanded to dilate the lesion. Then a second balloon catheter carrying a stent is inserted and expanded to place the stent at the location of the lesion. A single catheter can perform both functions, using the device and method of this invention. The catheter is inserted and the balloon is expanded to dilate the lesion. Then the balloon is deflated, the catheter removed and the balloon rewrapped. The device of this invention is then fitted over the balloon and the stent is transferred to the balloon as described above. The catheter is reinserted so that the balloon is again at the original lesion site. The balloon is expanded to expand and place the stent. Finally, the balloon is deflated and the catheter is removed, leaving the stent in place.

It is, therefore, an object of this invention to provide an improved device and method for placing stents onto any of a variety of delivery systems. Another object of the invention is to provide a stent mounting device that permits use of a single catheter for dilating a lesion and for placing a stent at the lesion site. A further object is to provide a device for mechanically applying a stent to a delivery system which does not require manual finger crimping of the stent. Yet another object is to provide a disposable device that can be preloaded with a stent for applying stents to balloon catheter. Other objects and advantages of the stent installation device and method of this invention will become apparent upon reading the following description of preferred embodiments.

BRIEF DESCRIPTION OF THE DRAWING

Details of the invention, and of preferred embodiments thereof, will be further understood upon reference to the drawing, wherein:

FIG. 7 is a side elevation view of the stent mounting device on a catheter body shaft;

FIG. 8 is a side elevation view of the stent mounting device positioned over a catheter balloon; and FIG. 9 is a side elevation view of the stent mounting device being axially split to release the balloon and stent assembly.

DETAILED DESCRIPTION OF PREFERRED EMBODIMENTS

Figure 1:
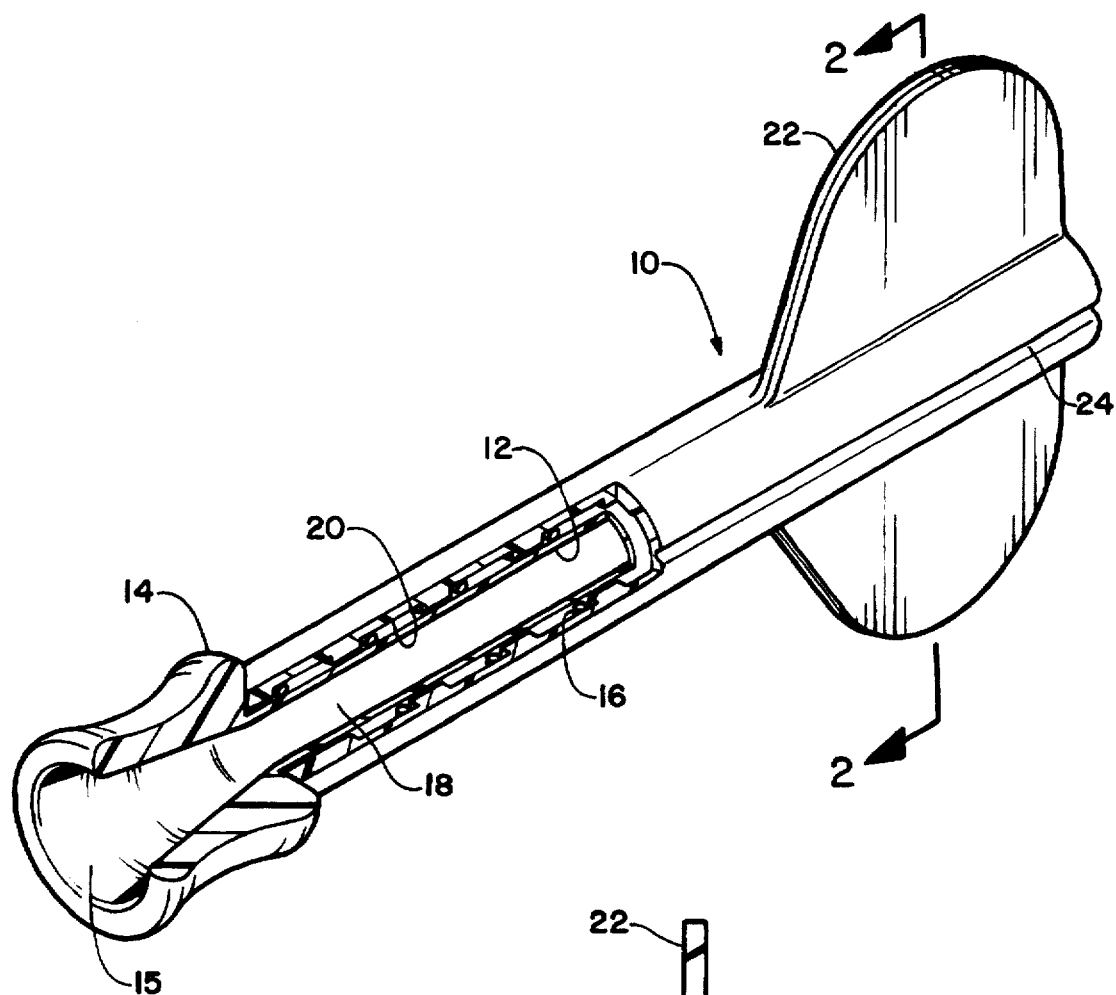
FIG. 1 is a perspective view, partly cut-away, or stent mounting device of this invention.
Figure 2:
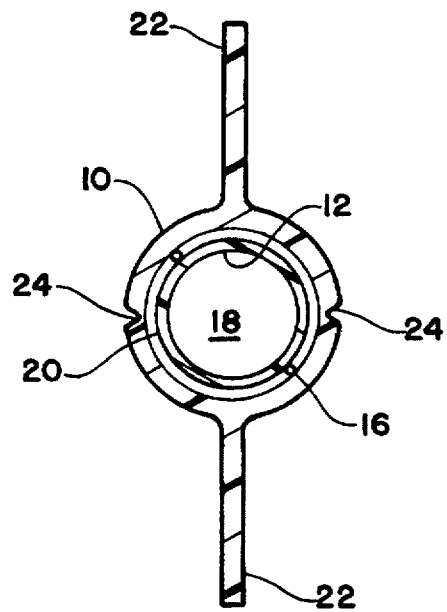
FIG. 2 is a section view taken on line 2—2 in FIG. 1.

As seen in FIGS. 1 and 2, the stent mounting device of this invention primarily comprises a body 10, a sleeve 12 having a knob 14 at one end and a stent 16. Body 10 has an axial aperture 18 therethrough for receiving sleeve 12. Knob 14 has any suitable shape to permit sleeve 12 to be easily pulled from axial aperture 18 during installation of a stent, as detailed below. The interior of knob 14 preferably has a conical entrance section 15. Sleeve 12 is preferably formed from a low friction material, such as fluorinated ethylene-propylene resins, polytetrafluoroethylene etc.

Recesses 20 are preferably provided in the wall of aperture 18 which are configured to receive stent 16 and help retain the stent in place. For example, with a commercially available Wiktor or Wiktor-I stent, recesses 20 would have a generally helical configuration to match the shape of the stent.

Longitudinal grooves 24, generally parallel to the axis of aperture 18, are formed along opposite sides of body 10. Body 10 may be formed from any suitable plastic material. Optimally, body 10 will be formed from a linearly oriented plastic material such as a mixture of polyurethane and polycarbonate which can be preferentially torn or split along lines parallel to the axis of aperture 18. Tabs 22 are provided at one end of body 10 to be grasped by a user's fingers and twisted or pulled apart to cause body 10 to split along grooves 24 on opposite sides of body 10.

The basic steps in manufacturing the stent mounting device are illustrated in FIGS. 3–6.

Figure 3:
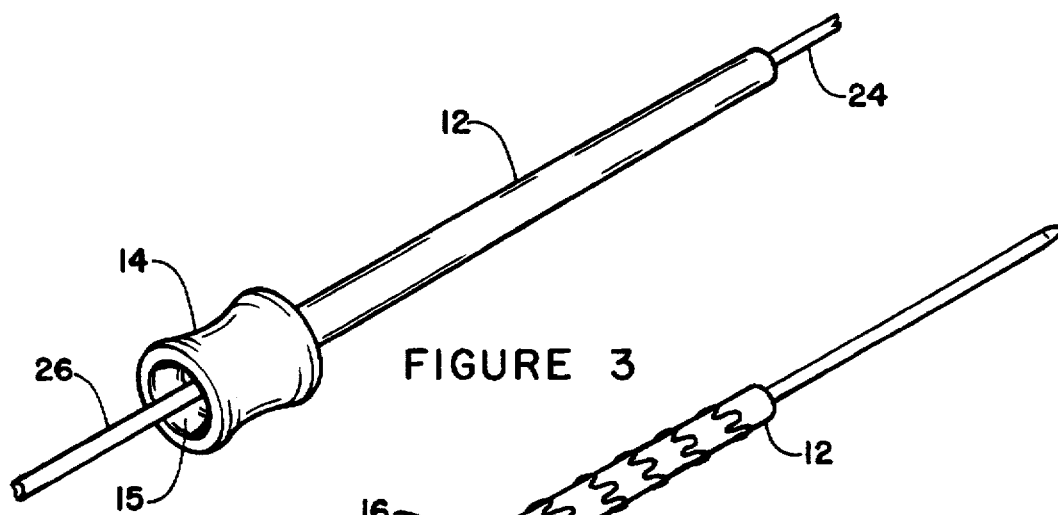
FIG. 3 is a perspective view of the sleeve portion of the stent mounting device on a supporting pin.

Initially, as seen in FIG. 3, a combination of sleeve 12 and knob 14 are formed from a suitable low friction material by any suitable process, such as injection molding. An elongated pin 26 having a diameter substantially equal to the inside diameter of sleeve 12 is inserted through sleeve 12 and knob 14 to support the sleeve.

Figure 4:
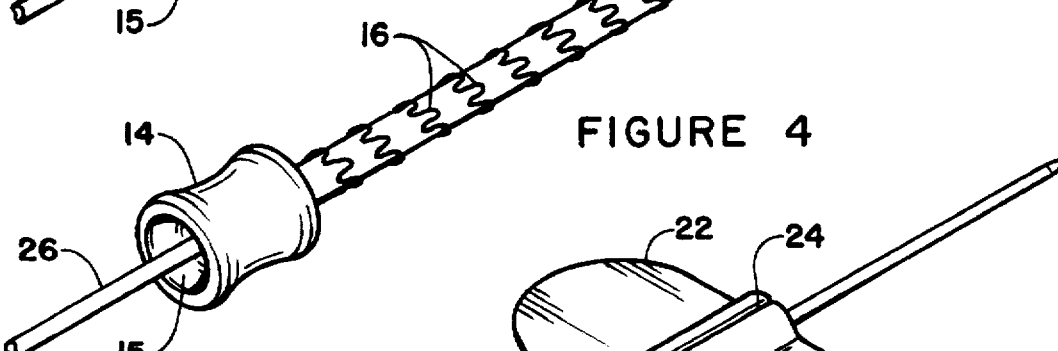
FIG. 4 is a perspective view of the sleeve portion of the stent mounting device carrying a stent.

FIG. 4 illustrates the placement of a stent 16 on sleeve 12. Preferably, stent 16 has a normal diameter slightly less than that of sleeve 12 and is expanded slightly as it is slid onto low friction sleeve 12. Stent 16 is thus held in place on sleeve 12 by spring forces.

Figure 5:
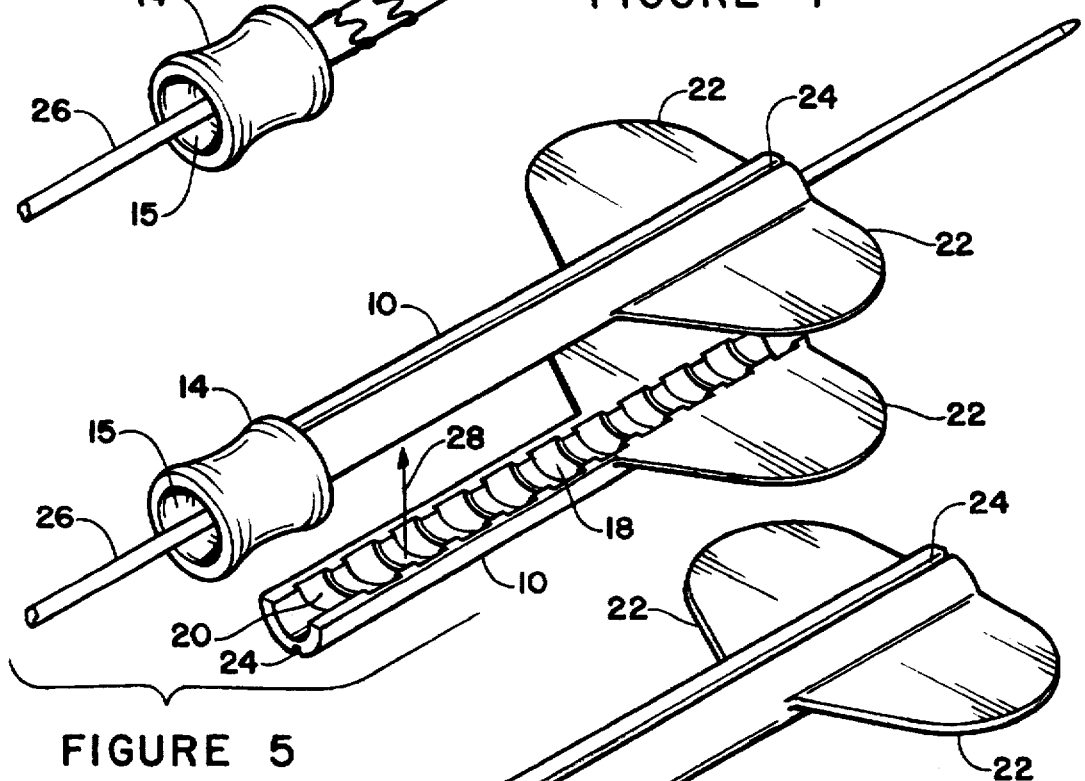
FIG. 5 is a perspective view showing the assembly of the body portion of the stent mounting device.
Figure 6:
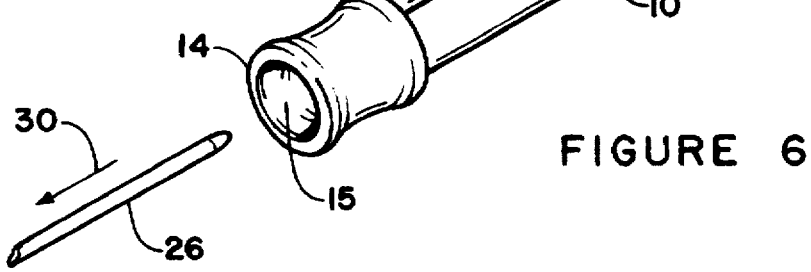
FIG. 6 is a perspective view showing the completed stent mounting device and removal of the support pin.

Next, as seen in FIG. 5, two halves of body 10, formed by any suitable process, such as injection molding, are brought together, as indicated by arrow 28, over stent 16 and sleeve 12 and bonded together. Any suitable bonding method may be used, such as adhesive, ultrasonic or thermal bonding may be used. Recesses 20 in the surfaces of the two halves of aperture 18 are configured to fit over stent 16.

In some cases, it may be preferred to form the tubular portion of body 10 by a method such as extrusion that can produce a body having loser strength in an axial direction than in a transverse direction and having a low resistance to splitting in the axial direction. Typically, such plastics are polymers having long chain lengths and little cross linking. Then, tabs 22 may be bonded to the body in any suitable manner.

When bonding of the body and tab halves together is complete, pin 26 is removed as indicated by arrow 30 and the stent mounting device is complete. These devices can be assembled in a factory environment, maintained in a sterile condition and shipped to the user in sterile packaging.

FIGS. 7–9 illustrate the steps in using the stent mounting device to mount a stent onto the balloon of a balloon catheter.

Initially, as seen in FIG. 7, the device is placed on a catheter body shaft 32. Catheter 32 carries a balloon 36. This catheter 32 could have been used to dilate a lesion at the site where the stent is to be placed, then removed and balloon 36 rewrapped for use in placing the stent.

As the device is moved along catheter 32, in the direction indicated by arrow 38 until balloon 36 begins to enter the conical entrance (not seen in FIGS. 7–9). Balloon 36 is wrapped and is slightly larger in cross section than is aperture 18, so that the balloon is compressed somewhat as it enters the aperture, until the position shown in FIG. 8 is reached. If body 10 is formed from a transparent material, the relative positions of stent 16 and balloon 36 can be observed during placement.

Once balloon 36 is properly placed, knob 14 is pulled in the direction indicated by arrow 40 until sleeve 12 is pulled out from between balloon 36 and stent 16. Since sleeve 12 is formed from a low friction material, neither the balloon nor stent is disturbed by movement of sleeve 12.

Finally, tabs 22 are grasped by the user's fingers and twisted and/or pulled apart, as indicated by arrows 40 in FIG. 9, until body 10 splits along grooves 24. The stent is then held in place on the balloon by a combination of elastic contraction of the stent occurring when sleeve 12 is removed and the compression of balloon 36 that occurred when forced through conical entrance 15. While not necessary, ends of stent 16 could be lightly crimped by finger pressure, if desired.

While certain specific relationships, materials and other parameters have been detailed in the above description of preferred embodiments, those can be varied, where suitable, with similar results. Other applications, variations and ramifications of the present invention will occur to those skilled in the art upon reading the present disclosure. Those are intended to be included within the scope of this invention as defined in the appended claims.

I claim:

1. A device for mounting a stent on a delivery system which comprises:

an elongated body having an axial aperture therethrough;

a stent in said axial aperture in engagement with a wall of said aperture;

a sleeve of low friction material in said stent;

tubular entrance means having a proximal end secured to said sleeve and extending beyond an end of said axial aperture for axially moving said sleeve from said axial aperture; and means for permitting said body to be split along said axial aperture comprising grooves running substantially parallel to said axial aperture in an exterior surface of said body to remove said body from said stent.

2. The device according to claim 1 wherein said tubular entrance tapers from a wider distal end to a narrower proximal end for receiving an end of a delivery means and guiding said delivery means into said axial aperture.

3. The device according to claim 1 wherein said delivery means is a balloon catheter.

4. The device according to claim 1 wherein said body is formed from a material having less resistance to splitting in a direction substantially parallel to said axial aperture than in a direction transverse thereto.

5. The device according to claim 1 further including tabs secured to said body for gripping by a user's fingers in splitting said body.

6. The device according to claim 1 further including recesses in an interior wall of said aperture, said recesses configured to receive said stent therein.

7. The device according to claim 1 wherein said sleeve is formed from a low friction material selected from the group consisting of fluorinated ethylene-propylene resins, polytetrafluoroethylene and mixtures and copolymers thereof.

8. A device for mounting a stent on a balloon catheter which comprises:

elongated body means having an axial aperture therethrough for receiving a stent;

a stent within said elongated aperture in engagement with a wall of said axial aperture;

retaining means in said axial aperture for restraining said stent against axial movement relative to said axial aperture;

tubular sleeve means formed from low friction material within and in pressure contact with said stent;

entrance means secured to said sleeve for guiding a balloon catheter into said axial aperture and for manually withdrawing said sleeve from said axial aperture; and means for splitting said body along said axial aperture comprising grooves running substantially parallel to said axial aperture in an exterior surface of said body and tabs secured to said body for gripping by a user's fingers in splitting said body.

9. The device according to claim 8 wherein said tubular entrance tapers from a wider distal end to a narrower proximal end for receiving an end of a delivery means and guiding said delivery means into said axial aperture.

10. The device according to claim 8 wherein said body is formed from a material having less resistance to splitting in a direction substantially parallel to said axial aperture than in a direction transverse thereto.

11. The device according to claim 8 further including recesses in an interior wall of said aperture, said recesses configured to receive said stent therein.

12. The device according to claim 8 wherein said sleeve is formed from a low friction material selected from the group consisting of fluorinated ethylene-propylene resins, polytetrafluoroethylene and mixtures and copolymers thereof.

13. A method of making an assembly for mounting a stent on a delivery system which comprises the steps of:

forming an elongated tubular sleeve having a handle portion at one end;

placing a stent over said sleeve;

forming two halves of a body having axial depressions therealong for cooperatively forming an axial aperture and having manually separable weakened lines along said body;

placing said sleeve on one of said halves; and bonding said halves together with said stent in said central aperture.

14. The method of making an assembly according to claim 13 including the further steps of inserting a pin having a cross section substantially equal to sleeve interior cross section into said sleeve prior to placing said stent over said sleeve and of removing said pin after bonding said halves together.

15. The method of making an assembly according to claim 14 wherein said tubular sleeve is formed with an outside diameter greater than stent inside diameter so that said stent is in tension over said sleeve.

16. The method of making an assembly according to claim 13 further including forming an outwardly extending tab on each said body half adjacent to an end of said body half.

17. The method of making an assembly according to claim 13 wherein said sleeve is formed from a low friction material selected from the group consisting of fluorinated ethylene-propylene resins, polytetrafluoroethylene and mixtures and copolymers thereof.

18. A method of mounting a stent on a delivery system which comprises the steps of:

providing a body having an axial aperture therethrough, a sleeve in said aperture and a stent between the outer surface of said sleeve and said aperture, said stent in tension over said sleeve;

inserting a delivery system into said sleeve, said delivery system's balloon in compression is said sleeve;

removing said sleeve from said axial aperture, leaving an assembly of said stent surrounding and in pressure contact with said delivery system; and tearing said body into two portions along lines that intersect the length of said aperture to release said assembly.

19. The method of mounting a stent on a delivery system according to claim 18 wherein said body has grooves on an external surface substantially parallel with said axial aperture and tabs extending from said body adjacent to one end of said body and said tearing is accomplished by pulling said tabs apart to split said body along said grooves.

20. The method of mounting a stent on a delivery system according to claim 18 wherein said sleeve includes a handle portion extending beyond said axial aperture having a generally conical central opening communicating with said sleeve, said delivery system's balloon is inserted through said central opening and compressed during entry into said sleeve and said sleeve is removed from said axial aperture by pulling on said handle.

21. The method of mounting a stent on a delivery system according to claim 18 wherein said sleeve is formed from a low friction material selected from the group consisting of fluorinated ethylene-propylene resins, polytetrafluoroethylene and mixtures and copolymers thereof.

* * * * *

UNITED STATES PATENT AND TRADEMARK OFFICE
CERTIFICATE OF CORRECTION

PATENT NO. : 5,630,830
DATED : May 20, 1997
INVENTOR(S) : Marcel A.E. Verbeek

It is certified that error appears in the above-identified patent and that said Letters Patent is hereby corrected as shown below:

Col. 6, Line 27: "wail" should be "wall"

Col. 5, Line 40: "loser" should be "looser"

Signed and Sealed this

Seventh Day of October, 1997

BRUCE LEHMAN

*Attest:*

*Attesting Officer*  *Commissioner of Patents and Trademarks*